United States Patent
Biller et al.

[11] Patent Number: 5,482,859
[45] Date of Patent: Jan. 9, 1996

[54] METHOD AND DEVICE FOR FEEDING GASEOUS SUBSTANCES INTO LIQUID MEDIA

[76] Inventors: Edmund Biller, Schmalzerstrasse 8, Raubling/Reischenhart, Germany, 8201; Eberhard Bock, Herwigredder 110a, Hamburg 56, Germany, 2000

[21] Appl. No.: 984,438

[22] PCT Filed: Feb. 25, 1993

[86] PCT No.: PCT/DE91/00608
   § 371 Date: Mar. 29, 1993
   § 102(e) Date: Mar. 29, 1993

[87] PCT Pub. No.: WO92/03534
   PCT Pub. Date: Mar. 5, 1992

[30] Foreign Application Priority Data

Aug. 28, 1990 [DE] Germany .................. 40 27 126.9

[51] Int. Cl.⁶ .............. C12S 5/00; C12M 1/12; C12M 1/04
[52] U.S. Cl. .................. 435/266; 435/294.1; 435/297.1; 95/129; 96/5; 96/8; 261/122.1; 423/235; 422/168
[58] Field of Search ............ 435/240.241, 240.242, 435/266, 243, 284, 311, 313, 818; 422/120, 122, 48, 168; 261/DIG. 28, 122.1, 100, 101, 102, 104, 105, 107; 55/16, 158; 210/638, 150, 321.6, 321.72, 321.75, 321.78, 321.79, 321.8, 321.84, 321.87, 321.88, 321.89; 96/4, 5, 6, 7, 8; 423/210, 235, 245.7; 95/90, 128, 129, 149, 230, 232

[56] References Cited

U.S. PATENT DOCUMENTS

| | | | |
|---|---|---|---|
| 3,184,395 | 5/1965 | Brewer | 195/80 |
| 3,894,954 | 7/1975 | Serur | 422/48 |
| 3,911,080 | 10/1975 | Mehl et al. | 423/210 |
| 3,941,662 | 3/1976 | Munder et al. | 435/284 |
| 4,098,852 | 7/1978 | Christen et al. | 261/104 |
| 4,355,636 | 10/1982 | Oetjen et al. | 261/104 |
| 4,416,993 | 11/1983 | McKeown | 435/243 |
| 4,564,373 | 1/1986 | Schmitz et al. | 55/16 |
| 4,670,234 | 6/1987 | Holter et al. | 423/235 |
| 4,900,448 | 2/1990 | Bonne et al. | 96/5 |
| 4,937,196 | 6/1990 | Wrasidlo et al. | 435/313 |
| 4,948,728 | 8/1990 | Stephanopoulos et al. | 435/313 |
| 5,077,208 | 12/1991 | Sublette | 435/266 |
| 5,110,741 | 5/1992 | Ohi et al. | 435/313 |

FOREIGN PATENT DOCUMENTS

| | | | |
|---|---|---|---|
| 0232975 | 8/1987 | European Pat. Off. | |
| 3309177 | 12/1988 | Japan | 435/284 |
| 0676677 | 2/1991 | Switzerland | 435/313 |
| WO89/12385 | 12/1989 | WIPO | |
| WO90/10690 | 9/1990 | WIPO | |

*Primary Examiner*—William H. Beisner
*Attorney, Agent, or Firm*—Pennie & Edmonds

[57] ABSTRACT

The device for feeding gaseous substances into liquid media comprises a number of hollow membrane bodies which are permeable to gas and contain the liquid media. These membranes are arranged with a distance between them in such a way that they can be reached by the gaseous substances. Such a device lends itself particularly to air purification. Gaseous substances such as nitrogen oxides can be converted with the aid of this device. According to the invention the device can also be used for pure or mixed cultures of various microorganisms whereby, above all, information about the toxicity of individual substances can be obtained.

14 Claims, 5 Drawing Sheets

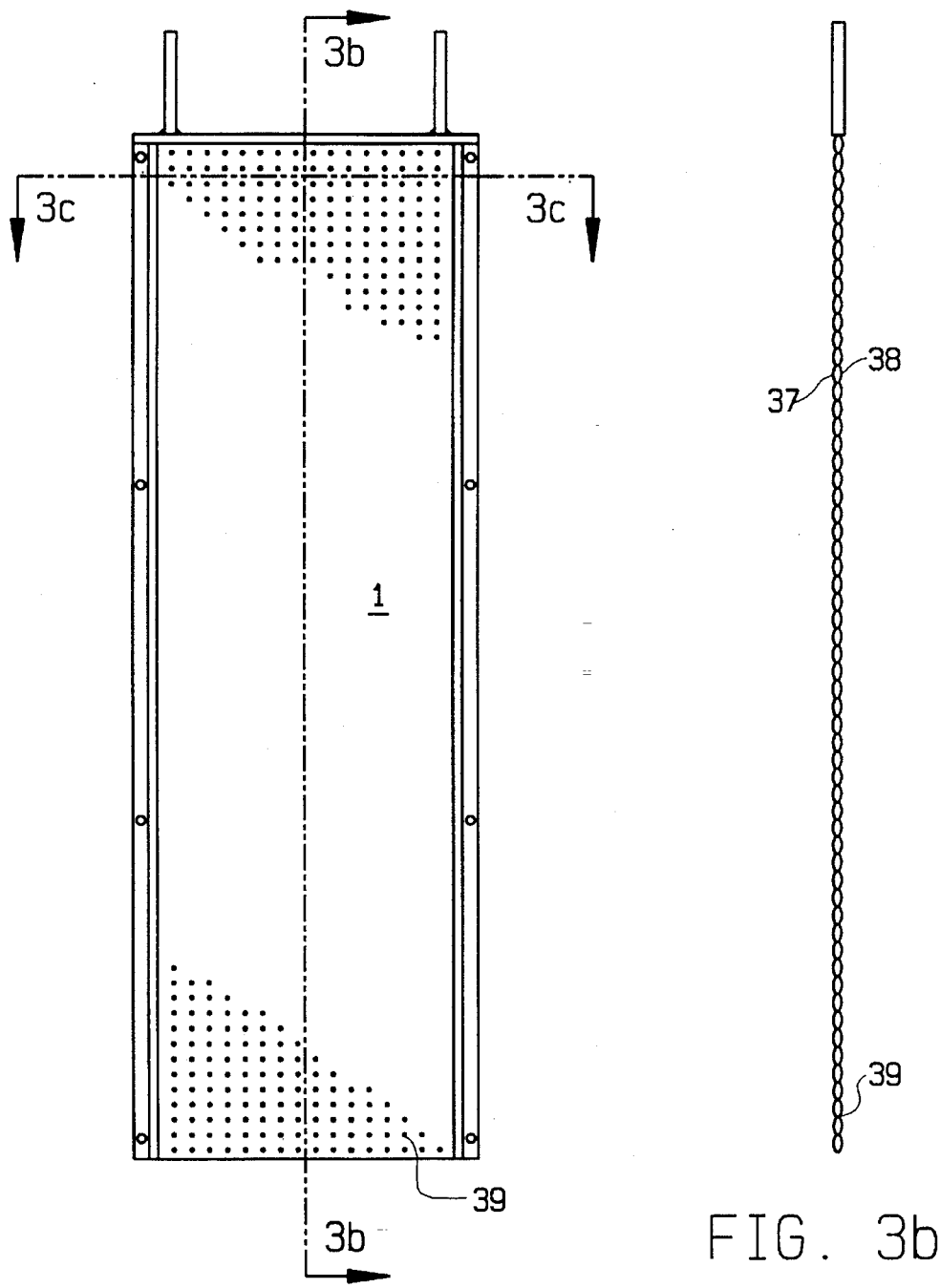
FIG. 3a
FIG. 3b
FIG. 3c

METHOD AND DEVICE FOR FEEDING GASEOUS SUBSTANCES INTO LIQUID MEDIA

BACKGROUND OF THE INVENTION

Frequently, especially for biological processes, gaseous substances have to be fed into liquid media. During such process the substance to be converted is at equilibrium between the two phases, which depends on the concentration of the respective substance in the gaseous phase. In many cases the concentrations of the gaseous substances are, however, that low that a sufficient conversion into the liquid phase is not or only insufficiently possible. This applies mostly to those cases where the solubility of the gas cannot be improved by increasing the pressure.

SUMMARY OF THE INVENTION

The conversion of gaseous substances into liquid media is especially important for biological systems. When supplying microorganisms such as bacteria or eucaryotic cells with gaseous substances, the substances have to be dissolved first in the watery medium containing the microorganisms. Only from this stage the substances can reach the microorganisms directly. Such systems, however, represent another difficulty; together with the gaseous substances unwanted foreign germs and toxic compounds are often transferred.

Object of the present invention is to provide a device for feeding gaseous substances into liquid media eliminating the disadvantages described above.

According to the invention the problem is solved by the arrangement of a number of hollow membrane bodies which are permeable to gas and contain the liquid media. These membranes are arranged with a distance between them in such a way that the gaseous substances can reach them.

BRIEF DESCRIPTION OF THE DRAWINGS

Further embodiments of the invention are described by the subclaims and are detailed below using the preferred embodiments shown in the drawings. It shows:

FIG. 1b Schematic cross-section of the device taken along 1b—1b of FIG. 1a

DETAILED DESCRIPTION OF THE INVENTION

Figure 1A:
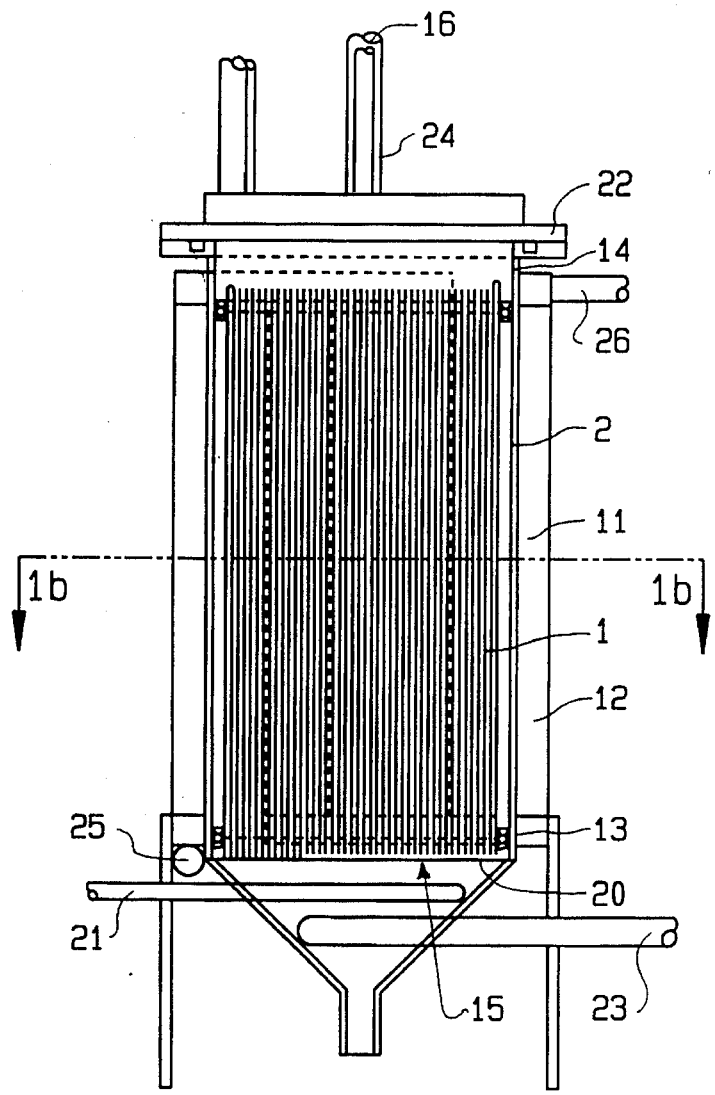
FIG. 1a Schematic side view of the device according to the invention
Figure 1B:
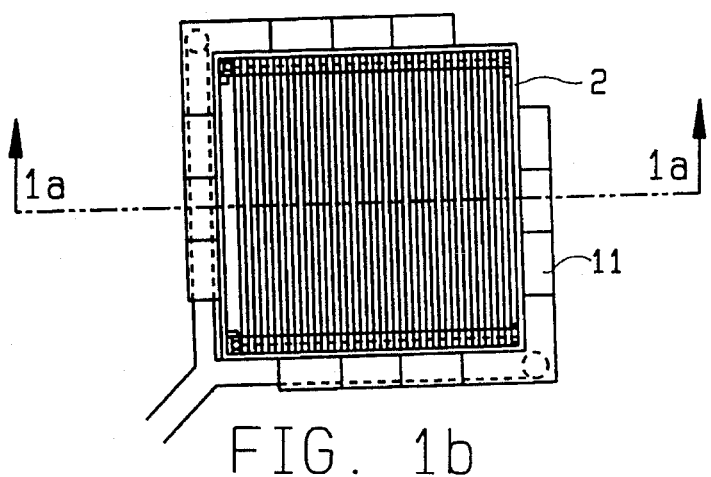

The device shown in FIG. 1 for carrying out the process according to the invention shows a preferred embodiment with the appearance of a reactor with a closed housing 2, where a number of hollow membrane bodies 1 is arranged with a distance between them. These hollow membrane bodies 1 form a membrane module, which is connected either fixed or detachable to housing 2. The individual hollow membrane bodies 1 are filled with a watery medium and a gaseous substance is streaming towards them. Preferably the medium flows parallel to the outer surfaces of the hollow membrane bodies so as to diffuse the gases as well as possible over the entire membrane surface. At the lower end 13 of housing 2 a bottom 20 with gas inlet openings 15 may be arranged. The medium streams via these gas inlet openings 15 to the hollow membrane bodies 1. To obtain a flow resistance as low as possible, bottom 20 can be omitted. Depending on the application the device may be directly installed in an existing gas stream. On the other hand, the medium to be cleaned may be transferred via transfer lines 21 to be fed into the device. After the gaseous medium has passed the hollow membrane bodies 1, the medium escapes at the top end 14 of housing 2. For this, cover 22 is provided with outlet openings. Alternatively, a central gas outlet 16 may be arranged.

Depending on the condition of the media to be converted it is advisable to provide an air conditioned environment for the hollow membrane bodies 1 to avoid drying out of the liquids contained in the hollow membrane bodies 1. For such an environment the relative humidity should preferably be kept between 50% and 100%. A defined quantity of conditioned air may be fed via feed lines 23 and the exhaust air may, for instance, escape via a centrally arranged exhaust air line 24. Through a temperature control device 12 arranged in jacket 11 the temperature of the entering media can be lowered up to near the dew point. As a result, a uniform high air humidity is produced. The temperature control device can be designed as a combined heating and cooling jacket and may be provided with a brine supply 25 and a brine drain 26. By these measures the temperature can be set to any value depending on the media inside the hollow membrane bodies. Under circumstances an overpressure or a depression may be advantageous when the gaseous medium has either a low or a high solubility.

Depending on the temperature and the relative humidity of the gaseous medium streaming in, a jacket insulation may be used so that the temperature in the device can be kept almost uniform and within the prescribed range. For temperatures below, for instance, 0° C. or above, for instance, 50° C. a jacket insulation should be used in addition to the temperature control device.

Figure 2A:
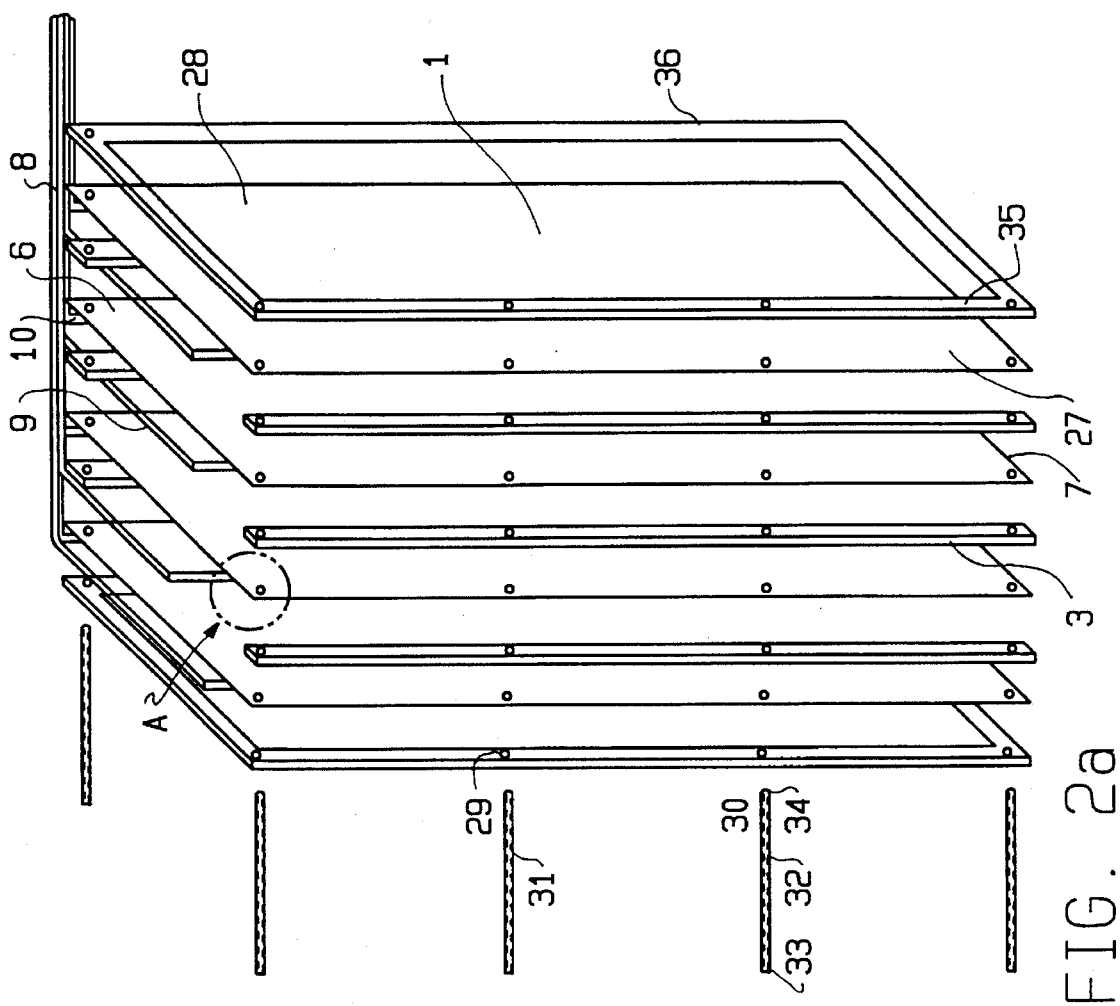
FIG. 2a Perspective side view of the arrangement of the individual hollow membrane bodies FIG. 2b Detail A, enlarged FIG. 3a Schematic side view of a hollow membrane body FIG. 3b Schematic longitudinal section of a hollow membrane body taken along lines 3b—3b of FIG. 3a FIG. 3c Schematic cross-section of a hollow membrane body taken along lines 3c—3c of FIG. 3a FIGS. 4a and 4b Schematic longitudinal section of a hollow membrane body FIG. 4c Schematic cross-section of a hollow membrane body FIG. 4d Detail B of a hollow membrane body FIG. 4e Detail C of a hollow membrane body FIG. 5 Cross-section of the arrangement of individual devices combined with each other

The arrangement of the hollow membrane bodies 1 is shown in FIG. 2a. The special configuration shows individual hollow membrane bodies 1 in the form of plates with pockets. The plates are arranged parallel to each other. Spacers 3 are arranged between the membranes 1. These spacers may have the form of a rod and any other cross-section, preferably rectangular. The spacers extend along the sides 27, 28 of the individual hollow membrane bodies 1 and have a cross-section allowing any distance between the individual hollow membrane bodies 1. Depending on the velocity of flow of the gaseous medium and depending on the kind of hollow membrane bodies 1 used, the distance may be approx. 2 mm or smaller or larger. The spacers 3 also serve as stabilizers of the complete the device. The spacers may be provided with bores 29, 30 to accommodate securing bolts 31, 32. Through threaded connections at the two ends 33, 34 of the securing bolts 31, 32 the hollow membrane bodies can be held together forming an easy to handle module. For further stabilization particularly the outer end spacers 35, 36 can be connected with each other. In a configuration not explained in detail spacers 3 are formed in such a way that they match with housing 2 serving as a bracket for the membrane module.

Figure 2B:
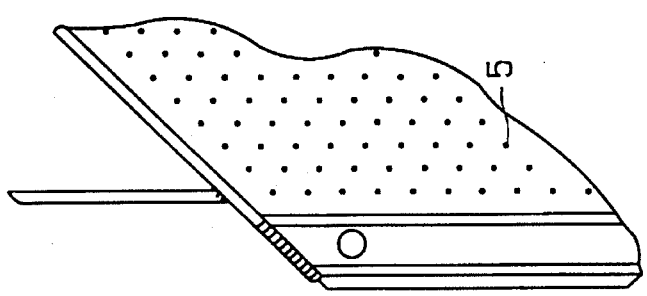

FIG. 2b shows detail A with individual raised spots 5 on the surface of the hollow membrane body. These raised spots can be obtained by reinforcing the membrane material and are to ensure the distance between two adjacent hollow membrane bodies over the total surface.

For reasons of refilling the hollow membrane bodies 1 share a common supply line 8 arranged at the top end 6, so that the hollow membrane bodies 1 can be filled up at any time. Therefore, each hollow membrane body is provided with a feed line 9 and an outlet line 10. The watery medium gets into the hollow membrane bodies 1 via feed line 9 and can be replaced via outlet line 10.

To avoid contamination by unwanted microorganisms the entire system can be sterilized. The hollow membrane bodies 1 may, for instance, be filled with water to be replaced later. Filling with water is to avoid that surfaces 37, 38 of the hollow membrane bodies stick to each other during sterilization. When the hollow membrane bodies 1 are intended to be used only once the feeding facilities may be omitted.

An individual hollow membrane body 1 is shown in FIGS. 3a to 3c. The preferred configuration of the hollow membrane body 1 is a flat design. In general, the hollow membrane body is provided with pockets and may have connections 39 between sides 37, 38 which, for instance, are produced by spot heat welds or bonds distributed over the entire hollow membrane body 1.

Figure 4A:
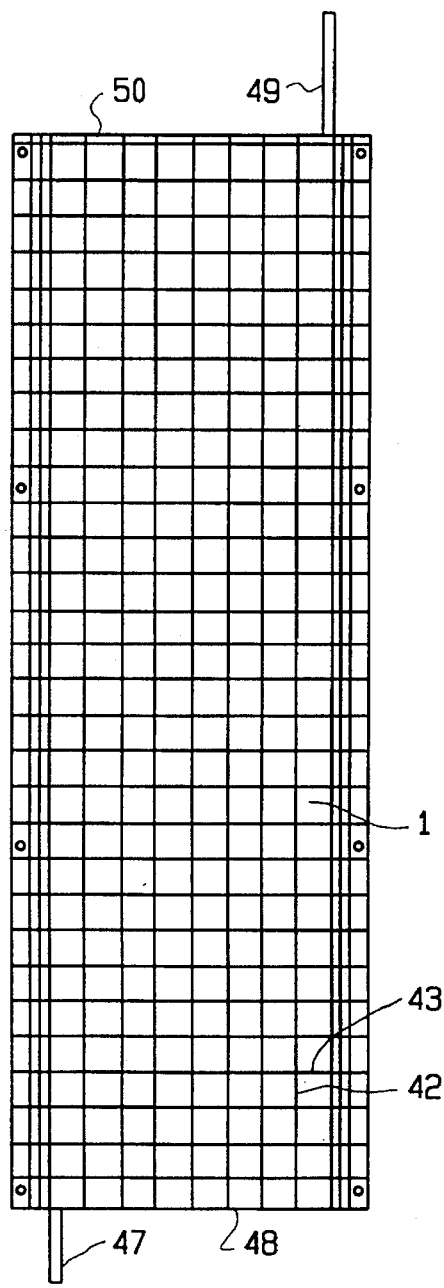
Figure 4B:
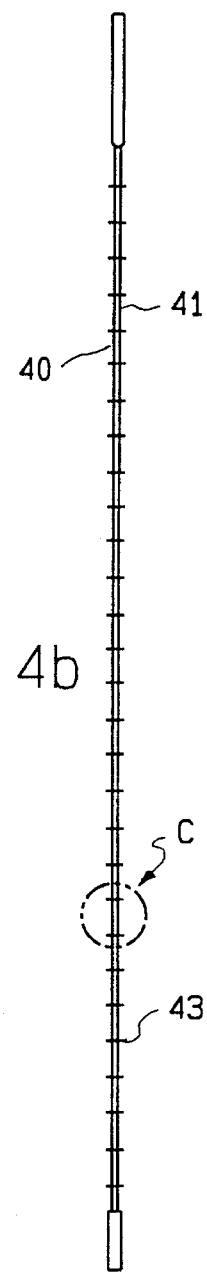
Figure 4C:
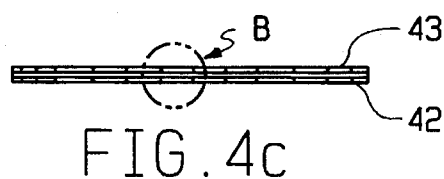
Figure 4D:
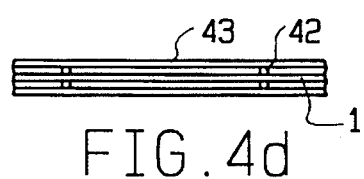
Figure 4E:
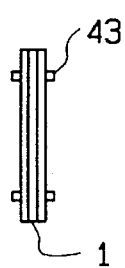
Figure 5:
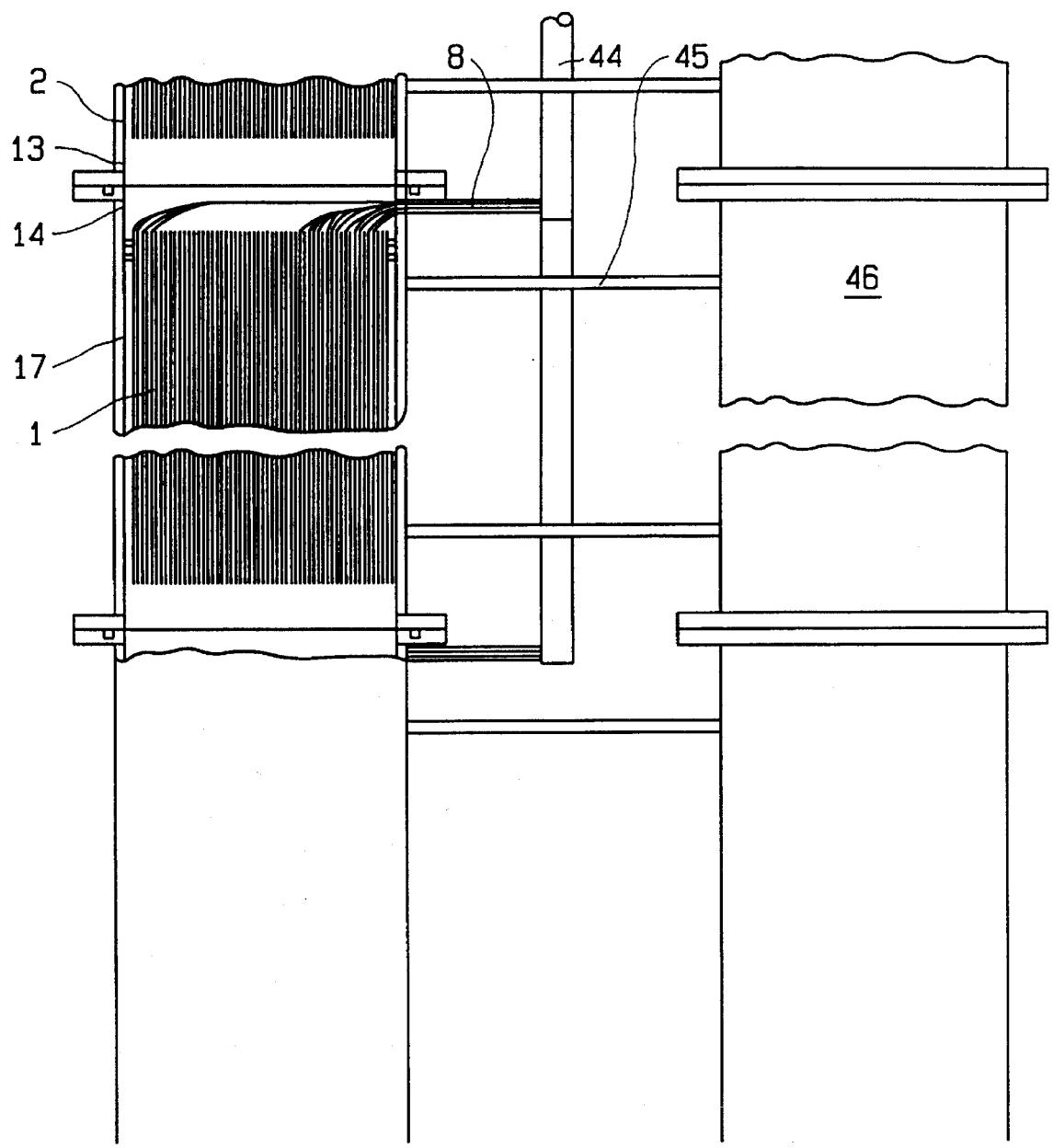

One possibility to reinforce the hollow membrane body 1 is that the outer sides 40, 41 are provided with thin reinforcement elements, for instance, longitudinal and transverse fibres 42, 43 made of a resistant material such as Teflon®. Such reinforcing elements may also be integrated in the membrane surfaces 37, 38 to obtain a membrane surface as smooth as possible. Such configuration of a hollow membrane body 1 is shown in FIGS. 4a to 4e. FIG. 4a also shows that the feed and outlet lines for refilling the hollow membrane body 1 may also be arranged on different sides of the hollow membrane body 1. A feed line 47, for instance, can be arranged at the bottom end. 48 and an outlet line 49 at the top end 50. By such arrangement it is possible to replace the contents of a hollow membrane body 1 nearly completely.

The hollow membrane bodies 1 are made of a material which is permeable to gas. The material can be resistant to a wide temperature range and can be sterilized, for instance, at 121° C. The material should be able to withstand mechanical loads and should resist chemical compounds to a high degree. A polyurethane film with a thickness of approx. 25 µm has been found to be especially advantageous. Such material is offered by several manufacturers and can, for instance, be bought under the tradename Walopur (Wolff Walsrode AG). The film may either be produced according to the longitudinal and/or the transverse production method. In addition to this, other materials permeable to gas such as silicone rubber may be used as well.

The hollow membrane bodies 1 may also have the form of a hose or a tube. In such case, the membrane module is composed of a bundle of hollow membrane bodies, which has the advantage of a flexible arrangement and, for instance, can be used in bent and angled air ducts.

When larger quantities of gaseous substances have to be converted the surface of the hollow membrane bodies 1 must be sufficiently large. This can, for instance, be reached when a large number of individual hollow membrane bodies is arranged side by side. Alternatively, several devices can be combined with each other to increase the quantity to be exchanged. Therefore, the lower end 13 of housing 2 is connected with the top end 14 of another housing 17, so that the gas can continuously flow through the membrane modules arranged one after the other. Between housings 17, 46, which are arranged side by side, additional connecting elements can be arranged. With such a combination of individual devices the supply lines 8 for individual membrane modules can be interconnected. For this, a common line 44 is provided with which all hollow membrane bodies 1 can be filled and emptied respectively. With the possibility to combine the individual devices it is possible, above all, to convert larger quantities of gaseous substances. When gaseous substances cannot be reduced to a certain percentage after streaming through individual or combined devices once, a recirculation is possible as well.

Application of the Device According to the Invention for Feeding Gaseous Substances into Watery Suspensions of Microorganisms With the device according to the invention microorganisms can be examined specifically. When subjecting pure or mixed cultures to gaseous substances, for instance, information on the utilization of various gases but especially on toxicities of individual substances can be obtained. The diffusion of gases over a large membrane surface results in a gentle admission to the microorganisms, which is of special importance for the treating of vegetable and animal cell cultures.

The device according to the invention is especially suitable for feeding such substances into watery suspensions of microorganisms which can be converted by the microorganisms contained in the suspension. Employing such method, for instance, gaseous sulphur compounds such as, for instance, hydrogen sulphide, carbon monoxide, carbon dioxide, gaseous hydrocarbons or/and nitrogen oxides can be removed from any kind of gas stream and converted.

Gaseous sulphur compounds such as hydrogen sulphide can be removed by, for instance, thiobacilli, whereas some other kinds of bacteria, for instance bacteria of the genera Pseudomonas, Alkaligenes, Nocardia and Methylomonas, can be used for the oxidation of carbon monoxide or hydrocarbons respectively.

For the removal of nitrogen oxides the hollow membrane bodies 1 can be filled with nitrifying bacteria, for instance of the genus Nitrobacter. These organisms oxidize nitrogen monoxide without the need of using any additional substrate. The nitrified bacteria, for instance, may be used in a watery solution, which is composed as follows:

TABLE 1

| Nutrient solution | |
|---|---|
| NaCl | 0.5 g/l |
| $MgSO_4 \cdot 7H_2O$ | 0.05 g/l |
| $KH_2PO_4$ | 0.15 g/l |
| $FeSO_4 \cdot 7H_2O$ | 0.15 g/l |
| $(NH_4)_6Mo_7O_{24} \cdot 4H_2O$ | 0.05 g/l |
| $CaCO_3$ | 0.01–1.0 g/l |

TABLE 1-continued

| Nutrient solution | |
| --- | --- |
| Value of pH | 7.4–8.0 |

The bacteria are added to the watery solution with a cell concentration to be as high as possible but at least $10^7$ cells/ml. The conversion of the substance is slower when the cell concentration is lower.

The same solution is also suitable for the cultivation of Methylomonas with which gaseous hydrocarbons such as methane can be removed. It can be seen frequently that various gaseous substances can be eliminated by using only one certain bacterial group.

The removal of nitrogen monoxide may also be achieved by using methylotrophic bacteria (e.g. genus Methylobacterium).

EXAMPLE 1

(Single Flow)

Being an experimental plant the device according to the invention accommodates a possible number of 29 hollow membrane bodies with pockets. Each membrane contains 25 ml of a bacterial suspension with $5 \times 10^8$ cells/ml and a natural isolate of the genus Methylobacterium. Methanol serves as substrate additive which has been added in a concentration of 1% to the mineral basis solution in accordance with the composition described in table 1. Subsequently, the device was subjected to an NO/air mixture with an NO concentration of 4.8 to 5.1 vpm and closed. After one hour the NO concentration inside the device had been reduced by 98%.

EXAMPLE 2

(Continuous Flow)

Furthermore, the microbial NO degradation rate was determined for a continuous flow with 29 hollow membrane bodies as described in Example 1. Before entry into the device and after having left the device the NO concentration of the gas was measured. The NO concentration of the used NO/air mixture was again 4.8 to 5.1 vpm. At a flow rate of 12 l/h the initial NO concentration was reduced by 40%. After increasing the flow rate by 100% to 24 l/h, 33% of the NO content was eliminated and at a flow rate of 48 l/h the NO content was reduced by even 25%.

Methanol oxidizing bacteria of the genera Ancylobacter and Rhenobacter were examined as well. These organisms were suspended like methylotrophic bacteria in a mineral medium without nitrogen source with 1% methanol as substrate. The examination revealed that when using the device according to the invention the measured NO consumption is directly depending on the quantity of bacteria. Representatives of the genus Rhenobacter have a higher specific activity than those of Ancylobacter. At 5° C. the NO consumption is considerably lower than at 28° C.

EXAMPLE 3

(Temperature Dependency)

The NO reduction as a function of temperature was examined with a suspension of facultative methylotrophic bacteria of the genus Methylobacterium. The experimental test arrangement was identical with that of Example 2. The flow rate of the air containing NO was 48 l/h. Table 2 shows that the maximum microbial NO degradation rate is between 10° and 15° C. At a temperature of 30° C. the NO degradation rate is lower than at 5° C.

TABLE 2

| NO reduction as a function of temperature | |
| --- | --- |
| Temperature | NO reduction |
| 5° C. | 20% |
| 10° C. | 35% |
| 15° C. | 32.5% |
| 20° C. | 32% |
| 25° C. | 25% |
| 30° C. | 12% |

As neither nitrite nor nitrate could be revealed—with the exception of nitrifying bacteria—an oxidative conversion of the used nitrogen monoxide is excluded. A reductive conversion of NO into $N_2O$ and $N_2$ is known as denitrification. In nature this process proceeds, however, under anaerobic conditions instead of the aerobic conditions prevailing during the experimental tests. An aerobic biological conversion of NO into $N_2O$ and $N_2$ is new. The conversion is not similar to the classic denitrification, as a cell growth could not be detected in the course of the tests, which is different to denitrification.

It has become known recently that NO is an important effector for the regulation of cell metabolism. NO covalently bonds iron-sulphur proteins forming a dinitro compound. In methylotrophic bacteria NO together with iron acts as an additional effector on the activity of the adenylate cyclase. Adenylate cyclase synthesizes cAMP, which regulates the synthesis for inducible enzymes. When much cAMP is inside a cell the transcription of inducible enzymes is possible. With NO the adenylate cyclase of methylotrophic bacteria and *Rhenobacter vacuolatum* is activated and that of guamilate cyclase is retarded. Hence, NO is a positive effector for enzyme induction of various bacteria.

It has to be assumed that bacteria with NO as an effector for the regulation of cell metabolism also regulate the concentration of NO themselves. When such bacteria are filled into the membranes of the device according to the invention the metabolic activities of these organisms can eliminate NO.

In the course of another experimental test the NO consumption was even increased by adding electron carriers to a cell suspension of Methylobacterium. In this way, the NO consumption of methanol oxidizing bacteria could be increased by adding $Fe^{3+}$- and PQQ (PQQ=Metoxatin= 2,7,9-tricarboxylic-1H-pyrrolo (2,3-f)-chinoline-4,5-dione). The methanol dehydrogenase of methylotrophic bacteria is not coupled with the reduction of NAD+ but with the electron transfer to Metoxatin. Quinone has a redox potential of $E'_0 = +120$ mV. Thus, NO is bonded to $Fe^{3+}$ and reduced to $N_2O$ with reduced PQQ. For this, the cells of methylotrophic bacteria provide the electrons from the methanol oxidation.

EXAMPLE 4

(Combination of Bacteria with Electron Carriers)

During preliminary experimental tests 25 ml of a cell suspension ($3.2 \times 10^8$ cells/ml) of Methylobacterium spec. were poured into a 1.3 l bottle with screw cap with 1% methanol and 4.85 vpm NO at a temperature of 28° C. After 6 h the NO consumption was measured.

TABLE 3

Influence of electron carriers on NO consumption

| Substances used | | NO consumption |
| --- | --- | --- |
| Control (without cells) | 2.35 vpm NO | |
| Cells | 1.75 vpm NO | 0.7 vpm |
| Cells + PQQ | 1.08 vpm NO | 1.39 vpm |
| Cells + PQQ + $Fe^{3+}$ − EDTA | 0.55 vpm NO | 1.91 vpm |

10 μM of PQQ and 10 mg of $Fe^{3+}$ − EDTA were used.

The results of this preliminary experimental test can be transferred to the device according to this invention. By feeding of watery suspensions of suitable microorganisms, and thus in the presence of electron carriers, increased NO conversion rates are reached.

Application of the Device according to the Invention for Feeding Gaseous Substances into Cell-free Solutions Based on the findings regarding the feeding of gaseous substances into suspending microorganisms in the presence of electron carriers further experimental tests were carried out with cell-free solutions to eliminate nitrogens. It was revealed that an NO consumption can also be reached when a watery solution is used which does not contain microorganisms. NO could be reduced with several reducing agents. NO, for instance, was bonded to $Fe^{3+}$ and reduced by an electron carrier.

EXAMPLE 5

(NO Reduction by Electron Carriers)

In the course of other preliminary experimental tests 25 ml of a mineral solution (value of pH 7.6) without bacteria and with 1 mM of ascotbit acid was poured into a 1.3 l bottle with screw cap with and without additives and in the presence of 4.26 vpm NO at a temperature of 28° C. Additives used were 10 μM PQQ and 10 μM $Fe^{3+}$-EDTA/l. Table 4 shows the results.

TABLE 4

Cell-free NO reduction

| Mixture | $NO_{tO}$ | $NO_{t=6h}$ | ΔNO | ΔNO - control |
| --- | --- | --- | --- | --- |
| Ascorbic acid | 4.26 | 3.89 | 0.37 | — |
| Ascorbic acid + PQQ | 4.26 | 2.40 | 1.86 | 1.49 |
| Ascorbic acid + PQQ + $Fe^{3+}$ − EDTA | 4.57 | 1.47 | 3.1 | 2.73 |

EXAMPLE 6

Using one each hollow membrane body according to the invention the experimental test described under Example 5 has, eventually, been repeated in such a way that one each pocket-like hollow membrane body was put into a gastight laboratory bottle with a volume of 1.3 l. For comparison reasons the membrane was filled with 1. Nb washing solution with a value of pH of 7.6 (control)

2. Nb washing solution with ascorbic acid (1 mM) and PQQ (10 μM)

3. Nb washing solution with ascorbic acid (1 mM), PQQ (10 μM) and $Fe^{3+}$-EDTA (10 mg/l)

4. Nb washing solution with ascorbic acid (1 mM) and $Fe^{3+}$-EDTA (10 mg/l)

The bottles were filled with an $NO/N_2$/compressed air mixture, closed gastight and placed in a dark room at 28° C. After six hours the NO concentrations in the bottles were determined. The results are shown in the table below.

TABLE 5

Cell-free NO reduction by membranes (values in vpm)

| Mixture | $NO_{tO}$ | $NO_{t=6h}$ | ΔNO | ΔNO - control |
| --- | --- | --- | --- | --- |
| Control | 4.54 | 2.50 | 2.04 | — |
| Ascorbic acid + PQQ | 4.88 | 2.01 | 2.87 | 0.83 |
| Ascorbic acid + PQQ + Fe | 4.91 | 2.07 | 2.84 | 0.80 |
| Ascorbic acid + Fe | 4.61 | 1.78 | 2.83 | 0.79 |

Based on the above-mentioned findings the device according to the invention can especially be used for the purification of air. By using this device, for instance, flue gas and exhaust from combustion plants and road tunnels can be cleaned.

We claim:

1. The method of feeding and conversion of a gaseous substance into a liquid media consisting of a watery suspension of microorganisms chosen from the group of microorganisms of the genera Pseudomonas, Alkaligenes, Nocardia, Methylomonas or of methylotrophic or nitrifying bacteria, comprising the steps of:

a) filling a number of hollow membrane bodies with said liquid media, said membrane bodies being of gas-permeable material and having a first end, a second end and an outer surface extending between said ends;

b) placing a plurality of said hollow bodies in side-by-side parallel spaced relation with respect to each other; and c) feeding a gaseous substance capable of said conversion into said liquid media simultaneously along the outer surfaces of each of said hollow bodies from one end thereof to the other.

2. The method for the purification of air defined by exhaust of combustion plants or road tunnels by feeding and conversion of said air into a liquid media, comprising the steps of:

a) filling a number of hollow membrane bodies with a liquid media consisting of a watery suspension of a liquid and air purifying substance chosen from the group consisting of ascorbic acid and electron carrying substances, said membrane bodies being of gas-permeable material and having a first end, a second end and an outer surface extending between said ends;

b) placing a plurality of said hollow bodies in side-by-side parallel spaced relation with respect to each other; and c) feeding said air to be purified by said conversion into said liquid media simultaneously along the outer surfaces of each of said hollow bodies from one end thereof to the other.

3. The method of feeding and conversion of a gaseous substance into a liquid media consisting of a watery suspension of a liquid and suspended substance chosen from the group consisting of ascorbic acid and electron carrying substances, comprising the steps of:

a) filling a number of hollow membrane bodies with said liquid media, said membrane bodies being of gas-permeable material and having a first end, a second end and an outer surface extending between said ends;

b) placing a plurality of said hollow bodies in side-by-side parallel spaced relation with respect to each other; and c) feeding a gaseous substance capable of said conversion into said liquid media simultaneously along the outer surfaces of each of said hollow bodies from one end thereof to the other.

4. The method for the purification of air defined by exhaust of combustion plants or road tunnels by feeding and conversion of said air into a liquid media, comprising the steps of:

a) filling a number of hollow membrane bodies with a liquid media consisting of a watery suspension of microorganisms chosen from the group of microorganisms of the genera Pseudomonas, Alkaligenes, Nocardia, Methylomonas or of methylotrophic or nitrifying bacteria, said membrane bodies being of gas-permeable material and having a first end, a second end and an outer surface extending between said ends;

b) placing a plurality of said hollow bodies in side-by-side parallel spaced relation with respect to each other; and c) feeding said air to be purified by said conversion into said liquid media simultaneously along the outer surfaces of each of said hollow bodies from one end thereof to the other.

5. Device for feeding gaseous substances along a predetermined direction of flow and into liquid aqueous media, comprising a) a plurality of hollow membrane bodies (1) constructed of gas-permeable material with each of said bodies having a first end and a second end defining a border of said body and a central section having an outer surface located inwardly of said border and with each of said bodies containing said liquid media, said bodies being arranged in side-by-side parallel spaced relation with respect to each other and parallel to said direction of flow of said gaseous substances; and b) means for directing said gaseous substances simultaneously along said outer surface of each of said membrane bodies from the first end thereof to the second end thereof.

6. Device according to claim 5, wherein the hollow membrane bodies (1) are made of gas-permeable film of polyurethane.

7. Device according to claim 5, wherein each of the hollow membrane bodies (1) includes an upper end (6) and a lower end (7) and are closed at the lower end (7) and connected to a common supply line (8) at the upper end (6).

8. Device according to claim 5, wherein the hollow membrane bodies (1) include both one feed and one outlet line (9, 10) for the liquid media.

9. Device according to claim 5, wherein the hollow membrane bodies (1) are developed as a module, said module being comprised of a plurality of said bodies connected together in said spaced relation and arranged in a housing (2) so that said plurality bodies can be removed from the housing as a single unit.

10. Device according to claim 9, wherein the housing (2) includes a jacket (11) with a temperature control system (12).

11. Device according to claim 9, wherein the housing (2) includes a lower end (13) with gas inlet openings (15) and an upper end (14) with gas outlet openings (16).

12. Device according to claim 5, wherein a plurality of said hollow membrane bodies (1) are developed as several single modules with each single module arranged in one of several housings (2), with each housing (2) having a lower end (13) and an upper end (14), so that each module can be removed from its associated housing and in that the several housings (2) are combined with one another whereby the lower end (13) of one housing (2) is joined with the upper end (14) of another housing (2), whereby single membrane modules are arranged one after the other with the interior of each of said bodies in one module connected to the interior of a separate one of the bodies in the next adjacent module.

13. Device for feeding gaseous substances along a predetermined direction of flow and into liquid aqueous media, comprising:

a) a plurality of hollow membrane bodies (1), each constructed of two opposed gas-permeable sheet materials with each of said sheet materials having a first end, a second end and side edges to define a border for said body and each of said bodies further having a central section, defined by said sheet materials, with opposite outer surfaces located inwardly of said border, and with each of said bodies being sealed along said first and second ends and side edges except for a filling opening and an outlet opening to define a hollow interior for containing said liquid media, said bodies being arranged in side-by-side parallel spaced relation with respect to each other;

b) means attaching said bodies together along at least part of some of said ends and edges with said outer surface of the central section of each body disposed in said spaced relation to define a single module consisting of a plurality of said bodies capable of being placed in and removed from a housing for said bodies; and c) means for directing said gaseous substances simultaneously in a direction parallel to and along said outer surfaces of each of said membrane bodies from the first end thereof to the second end thereof.

14. Device for feeding gaseous substances along a predetermined direction of flow and into liquid aqueous media, comprising:

a) a plurality of hollow membrane bodies (1), constructed of spaced gas-permeable materials with each of said bodies having a first end and a second end defining a border of said body and a central section having opposite outer surfaces located inwardly of said border, said gas-permeable materials being spaced from each other to define a hollow interior for each of said bodies and said liquid aqueous medium filling said hollow interior, said bodies being arranged in side-by-side parallel spaced relation with respect to each other and parallel to said direction of said gaseous substances; and b) means for directing said gaseous substances simultaneously along each of said opposite outer surfaces of each of said membrane bodies from the first end thereof to the second end thereof.

* * * * *